United States Patent
Pagès et al.

(10) Patent No.: US 9,833,794 B2
(45) Date of Patent: Dec. 5, 2017

(54) SYSTEM AND METHOD FOR AUTOMATED PLATELET WASH

(71) Applicant: Haemonetics Corporation, Braintree, MA (US)

(72) Inventors: Etienne Pagès, Cessy (FR); Dominique Uhlmann, Abington, MA (US); Matthew Murphy, Marshfield, MA (US)

(73) Assignee: Haemonetics Corporation, Braintree, MA (US)

( * ) Notice: Subject to any disclaimer, the term of this patent is extended or adjusted under 35 U.S.C. 154(b) by 454 days.

(21) Appl. No.: 14/337,637

(22) Filed: Jul. 22, 2014

(65) Prior Publication Data

US 2014/0329656 A1 Nov. 6, 2014

Related U.S. Application Data

(62) Division of application No. 13/883,518, filed as application No. PCT/US2010/056722 on Nov. 15, 2010, now Pat. No. 8,808,978.

(Continued)

(51) Int. Cl.
*B04B 13/00* (2006.01)
*B04B 15/06* (2006.01)
(Continued)

(52) U.S. Cl.
CPC ........... *B04B 15/06* (2013.01); *A61M 1/3692* (2014.02); *A61M 1/3693* (2013.01);
(Continued)

(58) Field of Classification Search
CPC ...... B04B 15/06; B04B 11/04; A61M 1/3692; A61M 1/3693; A61M 1/0281; C12N 5/0644
See application file for complete search history.

(56) References Cited

U.S. PATENT DOCUMENTS

| 1,025,059 A | 4/1912 | Hatton et al. |
| 1,611,725 A | 12/1926 | Degerth et al. |

(Continued)

FOREIGN PATENT DOCUMENTS

| CN | 1216527 | 8/2005 | ............... A01N 1/02 |
| CN | 1785330 | 6/2006 | ............... B04B 5/04 |

(Continued)

OTHER PUBLICATIONS

Azuma et al., "Reduction in adverse reactions to platelets by the removal of plasma supernatant and resuspension in a new additive solution (M-sol)," *Transfus.*, vol. 49, No. 2, pp. 214-218 (Feb. 2009).

(Continued)

*Primary Examiner* — Timothy Cleveland
(74) *Attorney, Agent, or Firm* — Sunstein Kann Murphy & Timbers LLP

(57) ABSTRACT

A method for washing platelets includes introducing anti-coagulant into a platelet product container, drawing re-anticoagulated platelet product from the platelet product container, and introducing it into a centrifuge bowl. The centrifuge bowl separates the platelets from the supernatant in which they are suspended. The method then washes the platelets by introducing wash solution into the centrifuge bowl. As the wash solution is introduced into the bowl, it displaces the supernatant from the bowl and into a waste container. The method then introduces platelet additive solution into the centrifuge bowl, which displaces the wash solution from the centrifuge bowl and into the waste container and further wash the platelets. The method then repeatedly accelerates and decelerates the centrifuge bowl to resuspend the platelets in the platelet additive solution.

13 Claims, 6 Drawing Sheets

Related U.S. Application Data

(60) Provisional application No. 61/410,738, filed on Nov. 5, 2010.

(51) Int. Cl.
*A61M 1/36* (2006.01)
*C12N 5/078* (2010.01)
*B04B 11/04* (2006.01)
*A61M 1/02* (2006.01)

(52) U.S. Cl.
CPC ........... *A61M 1/3696* (2014.02); *B04B 11/04* (2013.01); *B04B 13/00* (2013.01); *C12N 5/0644* (2013.01); *A61M 1/0281* (2013.01)

(56) References Cited

U.S. PATENT DOCUMENTS

| | | | |
|---|---|---|---|
| 2,087,778 A | 7/1937 | Nelin et al. | 210/64 |
| 2,661,150 A | 12/1953 | Abbott, Jr. | 233/27 |
| 2,750,107 A | 6/1956 | More | 233/2 |
| 2,792,172 A | 5/1957 | Tait | 233/2 |
| 3,096,283 A | 7/1963 | Hein | 233/20 |
| 3,145,713 A | 8/1964 | Latham | 128/214 |
| 3,211,368 A | 10/1965 | Shanely et al. | 233/1 |
| 3,239,136 A | 3/1966 | Hein | 233/20 |
| 3,244,362 A | 4/1966 | Hein | 233/27 |
| 3,244,363 A | 4/1966 | Hein | 233/28 |
| 3,409,213 A | 11/1968 | Latham, Jr. | 233/21 |
| 3,456,875 A | 7/1969 | Hein | 233/24 |
| 3,489,145 A | 1/1970 | Judson et al. | 128/214 |
| 3,565,330 A | 2/1971 | Latham, Jr. | 233/21 |
| 3,655,058 A | 4/1972 | Novak | 210/360 |
| 3,737,096 A | 6/1973 | Jones et al. | 233/19 A |
| 3,774,840 A | 11/1973 | Boatright | 233/14 R |
| 3,987,961 A | 10/1976 | Sinn et al. | 233/27 |
| 4,007,871 A | 2/1977 | Jones et al. | 233/27 |
| 4,010,894 A | 3/1977 | Kellogg et al. | 233/27 |
| 4,014,497 A | 3/1977 | Spiewok et al. | 233/20 R |
| 4,040,965 A | 8/1977 | Kohlheb | 210/297 |
| 4,056,224 A | 11/1977 | Lolachi | 233/14 R |
| 4,082,217 A | 4/1978 | Westberg | 233/25 |
| 4,086,924 A | 5/1978 | Latham, Jr. | 128/214 R |
| 4,140,268 A | 2/1979 | Lacour | 233/1 |
| 4,142,670 A | 3/1979 | Ishimaru et al. | 233/20 R |
| 4,151,844 A | 5/1979 | Cullis et al. | 128/214 R |
| 4,197,847 A | 4/1980 | Djerassi | 128/214 R |
| 4,285,464 A | 8/1981 | Latham, Jr. | 233/26 |
| 4,300,717 A | 11/1981 | Latham, Jr. | 233/1 A |
| 4,303,193 A | 12/1981 | Latham, Jr. | 233/23 A |
| 4,321,921 A | 3/1982 | Laszczower | 128/276 |
| 4,387,848 A | 6/1983 | Kellogg et al. | 494/81 |
| 4,416,654 A | 11/1983 | Schoendorfer et al. | 494/10 |
| 4,425,114 A | 1/1984 | Schoendorfer et al. | 604/7 |
| 4,430,072 A | 2/1984 | Kellogg et al. | 494/45 |
| 4,447,221 A | 5/1984 | Mulzet | 494/45 |
| 4,457,747 A | 7/1984 | Tu | 604/4 |
| 4,464,167 A | 8/1984 | Schoendorfer et al. | 604/6 |
| 4,466,888 A | 8/1984 | Verkaart | 210/232 |
| 4,482,342 A | 11/1984 | Lueptow et al. | 494/21 |
| 4,530,691 A | 7/1985 | Brown | 494/45 |
| 4,534,863 A | 8/1985 | Bacon et al. | 210/232 |
| 4,643,714 A | 2/1987 | Brose | 604/4 |
| 4,647,279 A | 3/1987 | Mulzet et al. | 494/45 |
| 4,680,025 A | 7/1987 | Kruger et al. | 604/6 |
| 4,684,361 A | 8/1987 | Feldman et al. | 494/41 |
| 4,692,136 A | 9/1987 | Feldman et al. | 494/38 |
| 4,708,712 A | 11/1987 | Mulzet | 494/45 |
| 4,713,176 A | 12/1987 | Schoendorfer et al. | 210/645 |
| 4,734,089 A | 3/1988 | Cullis | 494/27 |
| 4,740,202 A | 4/1988 | Stacey et al. | 604/119 |
| 4,740,313 A | 4/1988 | Schoendorfer et al. | 210/651 |
| 4,755,300 A | 7/1988 | Fischel et al. | 210/650 |
| 4,767,396 A | 8/1988 | Powers | 494/60 |
| 4,795,419 A | 1/1989 | Yawn et al. | 494/84 |
| 4,795,448 A | 1/1989 | Stacey et al. | 604/319 |
| 4,804,363 A | 2/1989 | Valeri | 604/6 |
| 4,806,247 A | 2/1989 | Schoendorfer et al. | 210/321.18 |
| 4,806,252 A | 2/1989 | Brown et al. | 210/744 |
| 4,808,307 A | 2/1989 | Fischel et al. | 210/321.68 |
| 4,850,995 A | 7/1989 | Tie et al. | 604/6 |
| 4,869,812 A | 9/1989 | Schoendorfer et al. | 210/321.63 |
| 4,871,462 A | 10/1989 | Fischel et al. | 210/651 |
| 4,876,013 A | 10/1989 | Shmidt et al. | 210/650 |
| 4,889,524 A | 12/1989 | Fell et al. | 494/12 |
| 4,911,833 A | 3/1990 | Schoendorfer et al. | 210/167 |
| 4,934,995 A | 6/1990 | Cullis | 494/45 |
| 4,940,543 A | 7/1990 | Brown et al. | 210/369 |
| 4,943,273 A | 7/1990 | Pages | 494/41 |
| 4,968,295 A | 11/1990 | Neumann | 604/6 |
| 4,983,156 A | 1/1991 | Knelson | 494/28 |
| 4,983,158 A | 1/1991 | Headley | 494/41 |
| 4,985,153 A | 1/1991 | Kuroda et al. | 210/782 |
| 4,994,188 A | 2/1991 | Prince | 210/636 |
| 5,039,401 A | 8/1991 | Columbus et al. | 210/117 |
| 5,045,048 A | 9/1991 | Kaleskas et al. | 494/41 |
| 5,098,372 A | 3/1992 | Jonsson | 604/5 |
| 5,100,372 A | 3/1992 | Headley | 494/41 |
| 5,100,564 A | 3/1992 | Pall et al. | 210/782 |
| 5,112,298 A | 5/1992 | Prince et al. | 604/6 |
| 5,114,396 A | 5/1992 | Unger et al. | 494/37 |
| 5,135,667 A | 8/1992 | Schoendorfer | 210/782 |
| 5,141,486 A | 8/1992 | Antwiler | 494/37 |
| 5,147,290 A | 9/1992 | Jonsson | 604/5 |
| 5,154,716 A | 10/1992 | Bauman et al. | 604/410 |
| 5,171,456 A | 12/1992 | Hwang et al. | 210/782 |
| 5,174,894 A | 12/1992 | Ohsawa et al. | 210/86 |
| 5,194,145 A | 3/1993 | Schoendorfer | 210/90 |
| 5,217,426 A | 6/1993 | Bacehowski et al. | 494/45 |
| 5,217,427 A | 6/1993 | Cullis | 494/45 |
| 5,234,403 A | 8/1993 | Yoda et al. | 604/4 |
| 5,234,608 A | 8/1993 | Duff | 210/806 |
| 5,254,248 A | 10/1993 | Nakamura | 210/321.67 |
| 5,273,517 A | 12/1993 | Barone et al. | 494/37 |
| 5,277,701 A | 1/1994 | Christie et al. | 604/4 |
| 5,298,016 A | 3/1994 | Gordon | 604/4 |
| 5,298,171 A | 3/1994 | Biesel | 210/739 |
| 5,300,060 A | 4/1994 | Nelson | 604/410 |
| 5,311,908 A | 5/1994 | Barone et al. | 137/881 |
| 5,316,540 A | 5/1994 | McMannis et al. | 494/37 |
| 5,318,512 A | 6/1994 | Neumann | 604/6 |
| 5,348,533 A | 9/1994 | Papillon et al. | 604/4 |
| 5,368,542 A | 11/1994 | McMannis et al. | 494/45 |
| 5,370,802 A | 12/1994 | Brown | 210/782 |
| 5,386,734 A | 2/1995 | Pusinelli | 73/863.21 |
| 5,387,174 A | 2/1995 | Rochat | 494/10 |
| 5,387,187 A | 2/1995 | Fell et al. | 604/6 |
| 5,403,272 A | 4/1995 | Deniega et al. | 604/4 |
| 5,405,308 A | 4/1995 | Headley et al. | 494/67 |
| 5,417,650 A | 5/1995 | Gordon | 604/4 |
| 5,427,695 A | 6/1995 | Brown | 210/805 |
| 5,431,814 A | 7/1995 | Jorgensen | 210/399 |
| 5,437,598 A | 8/1995 | Antwiler | 494/1 |
| 5,437,624 A | 8/1995 | Langley | 604/4 |
| 5,462,667 A | 10/1995 | Wollinsky et al. | 210/645 |
| 5,470,483 A | 11/1995 | Bene et al. | 210/741 |
| 5,478,479 A | 12/1995 | Herrig | |
| 5,484,396 A | 1/1996 | Naficy | 604/4 |
| 5,494,592 A | 2/1996 | Latham, Jr. et al. | 210/805 |
| 5,505,685 A | 4/1996 | Antwiler | 494/37 |
| 5,514,070 A | 5/1996 | Pages | 494/41 |
| 5,543,062 A | 8/1996 | Nishimura | 210/782 |
| 5,551,941 A | 9/1996 | Howell | 494/16 |
| 5,585,007 A | 12/1996 | Antanavich et al. | 210/782 |
| 5,607,579 A | 3/1997 | Latham, Jr. et al. | 210/195.1 |
| 5,614,106 A | 3/1997 | Payrat et al. | 210/767 |
| 5,649,903 A | 7/1997 | Deniega et al. | 604/6 |
| 5,651,766 A | 7/1997 | Kingsley et al. | 604/6 |
| 5,656,163 A | 8/1997 | Brown | 210/360.1 |
| 5,728,060 A | 3/1998 | Kingsley et al. | 604/4 |
| 5,733,253 A | 3/1998 | Headley et al. | 604/4 |
| 5,733,446 A | 3/1998 | Holm | 210/206 |
| 5,733,545 A | 3/1998 | Hood, III | 424/93.72 |
| 5,738,792 A | 4/1998 | Schoendorfer | 210/651 |

(56) References Cited

U.S. PATENT DOCUMENTS

| | | | |
|---|---|---|---|
| 5,753,428 A | 5/1998 | Yuasa et al. | 435/2 |
| 5,762,791 A | 6/1998 | Deniega et al. | 210/321.67 |
| 5,779,660 A | 7/1998 | Kingsley et al. | 604/6 |
| 5,783,085 A | 7/1998 | Fischel | 210/651 |
| 5,792,351 A | 8/1998 | Wehrle et al. | 210/321.67 |
| 5,792,372 A | 8/1998 | Brown et al. | 210/782 |
| 5,865,785 A | 2/1999 | Bischof | 604/5 |
| 5,882,289 A | 3/1999 | Sakota et al. | 494/41 |
| 5,899,874 A | 5/1999 | Jonsson | 604/4 |
| 5,919,125 A | 7/1999 | Berch | 494/67 |
| 5,964,724 A | 10/1999 | Rivera et al. | 604/4 |
| 5,980,760 A | 11/1999 | Min et al. | 210/782 |
| 6,007,725 A | 12/1999 | Brown | 210/739 |
| 6,027,904 A | 2/2000 | Devine et al. | 435/7.21 |
| 6,059,979 A | 5/2000 | Brown | 210/739 |
| 6,207,063 B1 | 3/2001 | Brown | 210/739 |
| 6,234,989 B1 | 5/2001 | Brierton et al. | 604/5.01 |
| 6,267,925 B1 * | 7/2001 | Pages | A01N 1/0247 210/739 |
| 6,296,602 B1 | 10/2001 | Headley | 494/37 |
| 6,464,624 B2 | 10/2002 | Pages | 494/36 |
| 6,558,307 B2 | 5/2003 | Headley | 494/37 |
| 6,582,349 B1 | 6/2003 | Cantu et al. | 494/1 |
| 6,743,192 B1 | 6/2004 | Sakota et al. | 604/6.01 |
| 6,773,413 B2 | 8/2004 | Keller et al. | 604/6.01 |
| 7,270,645 B2 | 9/2007 | Langley et al. | 604/6.01 |
| 7,306,555 B2 | 12/2007 | Dolecek et al. | 494/31 |
| 8,808,978 B2 | 8/2014 | Pagès et al. | 435/2 |
| 2001/0027156 A1 | 10/2001 | Egozy et al. | 494/37 |
| 2002/0062100 A1 | 5/2002 | Pierce et al. | 604/6.01 |
| 2003/0066807 A1 | 4/2003 | Suzuki | 210/782 |
| 2003/0094425 A1 | 5/2003 | Brandt et al. | 210/787 |
| 2003/0175150 A1 | 9/2003 | Grimm | 422/44 |
| 2004/0112808 A1 | 6/2004 | Takagi et al. | 210/143 |
| 2005/0139556 A1 | 6/2005 | Bischof | 210/787 |
| 2005/0147529 A1 | 7/2005 | Westberg et al. | 422/44 |
| 2005/0209522 A1 | 9/2005 | Tadokoro et al. | 600/508 |
| 2005/0234385 A1 | 10/2005 | Vandlik et al. | 604/6.03 |
| 2006/0205581 A1 | 9/2006 | Chammas | 494/16 |
| 2006/0287628 A1 | 12/2006 | Hirabuki | 604/6.01 |
| 2007/0243990 A1 | 10/2007 | Kolenbrander et al. | 494/37 |
| 2008/0076114 A1 | 3/2008 | Patzke | 435/4 |
| 2008/0199845 A1 | 8/2008 | Rosiello et al. | 435/2 |
| 2008/0281247 A1 | 11/2008 | Tadokoro et al. | 604/5.01 |
| 2008/0286379 A1 | 11/2008 | Wehling et al. | 424/530 |

FOREIGN PATENT DOCUMENTS

| | | | |
|---|---|---|---|
| CN | 1785530 | 6/2006 | B04B 5/04 |
| CN | 101557843 | 10/2009 | A61M 1/36 |
| EP | 0 128 683 | 12/1984 | A61M 1/03 |
| EP | 0 171 749 | 2/1986 | A61M 1/00 |
| EP | 0 208 061 | 1/1987 | A61M 1/34 |
| EP | 0 257 755 | 3/1988 | A61M 1/36 |
| EP | 0 308 407 | 4/1993 | A61M 1/36 |
| EP | 0 578 086 | 1/1994 | A61M 1/36 |
| EP | 0 619 145 | 10/1994 | B04B 9/12 |
| EP | 0 664 159 | 7/1995 | B04B 5/04 |
| EP | 0 754 461 | 1/1997 | A61K 35/14 |
| EP | 0 799 645 | 10/1997 | B04B 5/04 |
| EP | 0 885 619 | 12/1998 | A61M 1/36 |
| EP | 0 649 311 | 1/2000 | A61K 35/14 |
| EP | 0 992 256 | 4/2000 | A61M 1/38 |
| EP | 1 057 534 | 12/2000 | B04B 5/04 |
| EP | 1 146 895 | 11/2003 | A61K 38/19 |
| EP | 1 374 890 | 1/2004 | A61K 38/19 |
| EP | 1 925 327 | 5/2008 | A61M 1/02 |
| FR | 2 258 898 | 8/1975 | B04B 1/00 |
| GB | 2 047 110 | 11/1980 | A61M 1/03 |
| JP | 59-006952 | 1/1984 | B04B 5/00 |
| JP | 59-069166 | 4/1984 | B04B 11/00 |
| JP | 07-075746 | 3/1995 | B04B 1/02 |
| JP | 08-131539 | 5/1996 | A61M 1/02 |
| JP | 09-192215 | 7/1997 | A61M 1/02 |
| JP | 2002-531471 | 9/2002 | A01N 1/00 |
| JP | 2013/514863 | 5/2013 | A61M 1/34 |
| SU | 660718 | 5/1979 | B04B 5/00 |
| SU | 762982 | 9/1980 | B04B 5/04 |
| SU | 114098 | 3/1985 | B04B 5/00 |
| SU | 1146098 | 3/1985 | B04B 5/00 |
| WO | WO 85/02561 | 6/1985 | B04B 1/10 |
| WO | WO 87/06472 | 11/1987 | A61M 1/36 |
| WO | WO 90/00059 | 1/1990 | A61K 35/14 |
| WO | WO 90/07383 | 7/1990 | B04B 7/08 |
| WO | WO 93/21935 | 11/1993 | A61K 35/14 |
| WO | WO 94/06535 | 3/1994 | B01D 33/00 |
| WO | WO 96/11747 | 4/1996 | B04B 5/04 |
| WO | WO 96/33023 | 10/1996 | B04B 5/04 |
| WO | WO 00/33653 | 6/2000 | A01N 1/02 |
| WO | WO 00/44398 | 8/2000 | A61K 38/19 |
| WO | WO 01/38495 | 5/2001 | C12N 5/06 |
| WO | WO 2006/029233 | 3/2006 | A01N 1/02 |
| WO | WO 2006/044790 | 4/2006 | C12N 5/08 |
| WO | WO 2007/047687 | 4/2007 | A61K 35/14 |
| WO | WO 2008/079611 | 7/2008 | A61M 1/36 |
| WO | WO 2009/129131 | 10/2009 | A61M 1/36 |

OTHER PUBLICATIONS

Cazenave et al., "Chapter 2: Preparation of Washed Platelet Suspensions From Human and Rodent Blood," *Methods in Molecular Biology*, vol. 272: Platelets and Megakaryocytes, vol. 1: Functional Assays, pp. 13-28 (2004).

Grabmer et al., "Up to 21-day banked red blood cells collected by apheresis and stored for 14 days after automated wash at different times of storage," *Vox Sanguinis*, vol. 90, pp. 40-44 (2006).

Gulliksson, H., "Additive solutions for the storage of platelets for transfusion," *Transfus. Med.*, vol. 10, pp. 257-264 (2000).

Hirayama et al., "Storage of platelets in a novel additive solution (M-sol), which is prepared by mixing solutions approved for clinical use that are not especially for platelet storage," *Transfus.*, vol. 47, pp. 960-965 (Jun. 2007).

Hirayama et al., "Comparison between in vitro qualities of platelets washed with commercially available additive solutions and those washed with M-sol," *Vox Sanguinis*, vol. 99, pp. 131-135 (2010).

Kalmin et al., "Platelet washing with a blood cell processor," *Transfus.*, vol. 22, No. 2, pp. 125-127 (1982).

Kelley et al., "Washing platelets in neutral, calcium-free, Ringer's acetate," *Transfus.*, vol. 49, pp. 1917-1923 (Sep. 2009).

Ringwald et al., "Washing platelets with new additive solutions: aspects on the in vitro quality after 48 hours of storage," *Transfus.*, vol. 46, pp. 236-243 (Feb. 2006).

Ringwald et al., "Collection of hyperconcentrated platelets with Trima Accel," *Vox Sanguinis*, vol. 90, No. 2, pp. 92-96 (2006).

Schoenfeld et al., "Platelet Activity in Washed Platelet Concentrates," *Anesth. Analg.*, vol. 99, No. 1, pp. 17-20 (Jul. 2004).

Shimizu et al., "Plasma-Depleted Platelet Concentrates Prepared with a New Washing Solution," *Vox* Sanguinis, vol. 64, pp. 19-23 (1993).

Sloand et al., "Preparation of IgA-deficient platelets," *Transfus.*, vol. 30, No. 4, pp. 322-326 (1990).

Tóth et al., "IgA Content of Washed Red Blood Cell Concentrates," *Vox Sanguinis*, vol. 74, No. 1, pp. 13-14 (1998).

Tynngard et al., "Platelet quality after washing: the effect of storage time before washing," *Transfusion*, vol. 50, pp. 2745-2752 (Dec. 2010).

Valbonesi et al., "Preparation and storage in Plasma-Lyte A of platelets collected with the cell separator CS3000 Plus equipped with the PLT30-separation and TNX6 collection chambers, " *Int. J. Artif. Organs*, vol. 18, No. 1, pp. 39-44 (Jan. 1995).

Valeri et al., "A multicenter study of in vitro and in vivo values in human RBCs frozen with 40-percent (wt/vol) glycerol and stores after deglycerolization for 15 days at 4° C. in AS-3: assessment of RBC processing in the ACP 215," *Transfus.*, vol. 41, pp. 933-999 (Jul. 2001).

Valeri et al., "The in vitro quality of red blood cells frozen with 40 percent (wt/vol) glycerol at -80° C. for 14 years, deglycerolized with

(56) References Cited

OTHER PUBLICATIONS the Haemonetics ACP 215, and stored at 4° C. in additive solution-1 or additive solution-3 for up to 3 weeks," *Transfus.*, vol. 44, pp. 990-995 (Jul. 2004).

Valeri et al., "Automation of the glycerolization of red blood cells with the high-separation bowl in the Haemonetics ACP 215 instrument," *Transfus.*, vol. 45, pp. 1621-1627 (Oct. 2005).

Vesilind et al., "Evaluation of a centrifugal blood cell processor for washing platelet concentrates," *Transfus.*, vol. 28, No. 1, pp. 46-51 (1988).

Vo et al., "Platelet washing to prevent recurrent febrile reactions to leucocyte-reduced transfusions, " *Transfus. Med.*, vol. 11, pp. 45-47 (Feb. 2001).

"Indication guidance for washed and replaced platelets and their preparation," Version II, available from: http://www.jstmct.or.jp/jstmct/Document/Guideline/Ref9-2.pdf, 3 pages (Feb. 2009).

Malte Kaden, Authorized officer European Patent Office, *International Search Report and Written Opinion of the International Searching Authority*—International Application No. PCT/US2010/056722, dated Aug. 22, 2011 (10 pages).

Second Patent Examination Dept. Japanese Patent Office, Official Action—Application No. 2013-537,650, dated Oct. 8, 2013 (2 pages)

Second Patent Examination Dept. Japanese Patent Office, Notification of Reason for Rejection—Application No. 2013-537,650, dated Oct. 8, 2013 (3 pages), [English Translation].

\* cited by examiner

SYSTEM AND METHOD FOR AUTOMATED PLATELET WASH

PRIORITY

This patent application claims priority from and is a divisional application of co-pending U.S. patent application Ser. No. 13/883,518, entitled "System and Method for Automated Platelet Wash," filed on Jul. 31, 2013, and naming Etienne Pagès, Dominique Uhlmann, and Matthew Murphy as inventors. U.S. application Ser. No. 13/883,518 claims priority from and is a National Phase filing of PCT/US2010/056722, filed on Nov. 15, 2010, and naming Etienne Pagès, Dominique Uhlmann, and Matthew Murphy as inventors. PCT application PCT/US2010/056722 claims priority from U.S. Provisional Patent Application Ser. No. 61/410,738, filed Nov. 5, 2010, entitled, "System and Method For Automated Platelet Wash," and naming Etienne Pagès, Dominique Uhlmann, and Matthew Murphy as inventors. The disclosures of each of the above applications are incorporated herein, in their entireties, by reference.

TECHNICAL FIELD

The present invention relates to systems and methods for washing collected platelets, and more particularly to system and methods for washing collected platelets in an automated and closed process.

BACKGROUND ART

Apheresis is a procedure in which individual blood components (e.g., platelets) can be separated and collected from whole blood temporarily withdrawn from a subject. Additionally, blood components such as platelets may be collected using a variety of other process. Once collected, these components may be stored and later transfused into patients. However, in some instances, the receiving patient may have adverse reactions (sometime severe) to the transfusion. For example, the occurrence of adverse reactions such as allergic reactions, anaphylactic reactions, and/or febrile nonhemolytic transfusion reactions (FNHTRs) to platelet concentrates (PCs) and/or platelet rich plasma (PRP) is well-documented. A large number of these adverse reactions are caused by the patients' sensitivity to the proteins contained within the plasma (e.g., the supernatant in which the platelets are suspended). Additionally, the plasma/supernatant may also contain a number of contaminates that are in solution with and/or suspended within the supernatant. These contaminates may increase the severity of the reactions and/or may cause additional reactions.

In order to reduce the occurrence of these reactions, various prior art systems "wash" the platelets to remove the plasma supernatant from the platelet concentrate and/or PRP prior to transfusion. For example, prior art systems may dilute the platelet product with saline solution within the platelet collection bag. Once diluted, prior art systems and methods then centrifuge the diluted platelet product in order to form a "platelet pellet" at the bottom of the bag. The pellet supernatant (e.g., the plasma) may then be removed, for example, using a whole blood separation press, and the platelets resuspended in a different solution. The dilution procedure must then be repeated multiple times (e.g., at least three times) in order to sufficiently remove the supernatant (e.g., the plasma) and proteins/contaminates. Once the supernatant and proteins have been sufficiently removed, the platelets may then be resuspended within a platelet additive solution. By essentially replacing the plasma supernatant with platelet additive solution, prior art methods are able to reduce the risk of adverse reaction.

However, prior art systems and methods like those described above are problematic for a variety of reasons. First, because prior art systems require multiple sterile docking steps (e.g., in order to repeat the washing procedure and to add the platelet additive solution), the product is not processed in a functionally closed manner which, in turn, increases the risk of contamination and reduces the length of time that the platelets can be stored. Additionally, manual processes inherently have a high risk of human error and the results may vary depending on the operator (e.g., they are not reproducible). Furthermore, the manual prior art procedures are labor intensive.

SUMMARY OF THE EMBODIMENTS

In accordance with one embodiment of the present invention, a method for washing platelets includes introducing anticoagulant into a platelet product container, and drawing anticoagulated platelet product from the container. The platelet product (e.g., platelet rich plasma) within the container may contain platelets suspended within a supernatant (e.g., plasma). The method may then introduce the anticoagulated platelet product into a centrifuge bowl which, in turn, separates the platelets from the supernatant. Once the platelets are separated from the supernatant, the method may then introduce wash solution (e.g., anticoagulated saline glucose solution) into the centrifuge bowl to displace the supernatant from the bowl (e.g., into a waste container), and introduce platelet additive solution into the centrifuge bowl to displace the wash solution from the centrifuge bowl (e.g., into the waste container).

After introducing the platelet additive solution and displacing the wash solution, the method may then "jog" the bowl by accelerating (e.g., for two second) and decelerating the centrifuge bowl (in the same direction or alternating between clockwise and counter-clockwise directions) multiple times (e.g., starting and stopping once and then repeating, for example, three times) to resuspend the platelets in the platelet additive solution. The method may then transfer the resuspended platelets and platelet additive solution to a platelet storage container.

In additional embodiments, the method may transfer a portion of the resuspended platelets and platelet additive solution from the centrifuge bowl to a platelet storage container and then, once again, repeat the accelerating and decelerating process at least once (e.g., four additional times). After repeating the accelerating and decelerating process, the method may then transfer the platelets and platelet additive solution remaining within the centrifuge bowl to the platelet storage container. The method may also add platelet additive solution to the washed-platelet storage container after the system transfers the remaining platelets and platelet additive solution to the washed-platelet container to achieve a predetermined washed-platelet volume and/or a predetermined washed-platelet yield.

In some embodiments, the method may introduce anticoagulant into the wash solution prior to introducing the wash solution into the centrifuge bowl. The method may also rinse the centrifuge bowl with platelet additive solution after the second jogging step, and transfer the platelet additive solution in the centrifuge bowl (e.g., the solution used for the rinse) to the platelet storage container.

In accordance with additional embodiments, the method may agitate the platelet product container (e.g., with a shaker) as anticoagulant is in introduced into the platelet product container. Additionally, the method may also transfer a portion of the resuspended platelets and platelet additive solution to the platelet storage container prior to initially jogging the centrifuge bowl.

In accordance with further embodiments of the present invention, a system for automated platelet washing may include (1) a sterile connection for connecting a platelet product container to the system and withdrawing platelet product from the container, (2) a centrifuge bowl, (3) a wash solution source, (4) a platelet additive solution source, and (5) a controller. The centrifuge bowl separates the platelet product into platelets and a supernatant, and may be configured to send the supernatant to a waste container. The wash solution source may be fluidly connected to the centrifuge bowl and configured to send wash solution to the centrifuge bowl. The platelet additive solution source may be fluidly connected to the centrifuge bowl and configured to send platelet additive solution to the centrifuge bowl. The controller controls the operation of the centrifuge bowl, and may accelerate (e.g., for two seconds) and decelerate the centrifuge bowl multiple times (e.g., four times) to resuspend the platelets within the platelet additive solution (e.g., after the platelet additive solution is added to the platelets and the supernatant is sent to the waste container). Accelerating and decelerating may include starting and stopping the bowl. In some embodiments, the controller may alternate starting the bowl in clockwise and counter-clockwise directions when accelerating and decelerating the centrifuge bowl.

The system may also include a washed-platelet storage container, and the system may transfer a portion of the resuspended platelets to the washed-platelet storage container after the controller accelerates and decelerates (e.g., starts and stops) the centrifuge bowl. In such embodiments, the controller may repeat the accelerating and decelerating of the centrifuge bowl after the portion of the resuspended platelets is transferred to the washed-platelet storage container. Additionally, the system may transfer the remaining platelets and platelet additive solution to the washed-platelet storage container after the controller repeats the accelerating and decelerating. The system may also include an anticoagulant source, and the system may introduce anticoagulant from the anticoagulant source into the platelet product container. In some embodiments, the controller may also be configured to add platelet additive solution to the washed-platelet storage container after the system transfers the remaining platelets and platelet additive solution to the washed-platelet container to achieve a predetermined washed-platelet volume and/or a predetermined washed-platelet yield.

In accordance with additional embodiments, a system for washing platelets may include (1) means for introducing anticoagulant into a platelet product container, (2) means for drawing anticoagulated platelet product from the platelet product container, (3) a centrifuge bowl, (4) means for introducing wash solution into the centrifuge bowl, (5) means for introducing platelet additive solution into the centrifuge bowl, and (6) a controller for controlling the operation of the centrifuge bowl. The platelet product may contain platelets suspended within a supernatant, and the centrifuge bowl may separate the platelets from the supernatant. As it enters the bowl, the wash solution may displace the supernatant from the bowl and into a waste container. Similarly, as the platelet additive solution enters the bowl, the platelet additive solution may displace the wash solution from the centrifuge bowl and into the waste container.

The controller may accelerate and decelerate the centrifuge bowl multiple times to resuspend the platelets within the platelet additive solution after the platelet additive solution has displaced the supernatant (e.g., contaminated supernatant) to the waste container. The system may also include means for transferring the resuspended platelets and platelet additive solution to a platelet storage container.

Some embodiments may also include means for transferring a portion of the resuspended platelets and platelet additive solution from the centrifuge bowl to a platelet storage container. In such embodiments, the controller may also be configured to repeat the accelerating and decelerating (e.g., stopping and starting) of the centrifuge bowl after the portion of the resuspended platelets is transferred to the platelet storage container. The system may also include means for transferring the remaining resuspended platelets and platelet additive solution from centrifuge bowl to the platelet storage container, and means for introducing anticoagulant into the wash solution prior to introducing the wash solution into the centrifuge bowl.

The controller may be further configured to alternate starting the bowl in clockwise and counter-clockwise directions when starting and stopping the centrifuge bowl. Additionally, the system may also include a shaker to agitate the platelet product container as anticoagulant is in introduced into the platelet product container. In some embodiments, the controller may also be configured to add platelet additive solution to the washed-platelet storage container after the system transfers the remaining platelets and platelet additive solution to the washed-platelet container to achieve a predetermined washed-platelet volume and/or a predetermined washed-platelet yield.

BRIEF DESCRIPTION OF THE DRAWINGS

The foregoing features of embodiments will be more readily understood by reference to the following detailed description, taken with reference to the accompanying drawings, in which.

DETAILED DESCRIPTION OF SPECIFIC EMBODIMENTS

Figure 1:
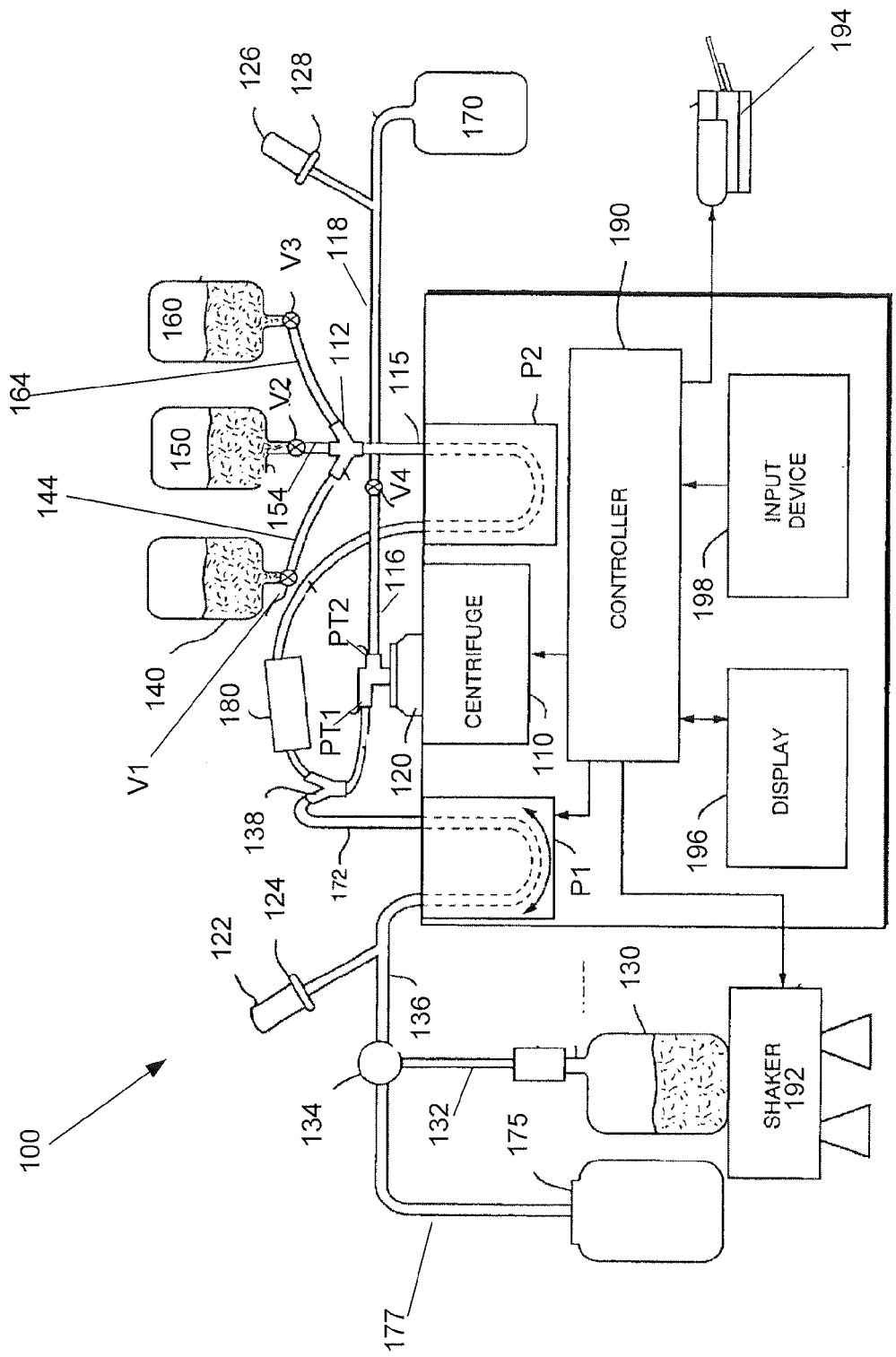
FIG. 1 is a schematic diagram of a platelet wash system, in accordance with one embodiment of the invention.
Figure 2:
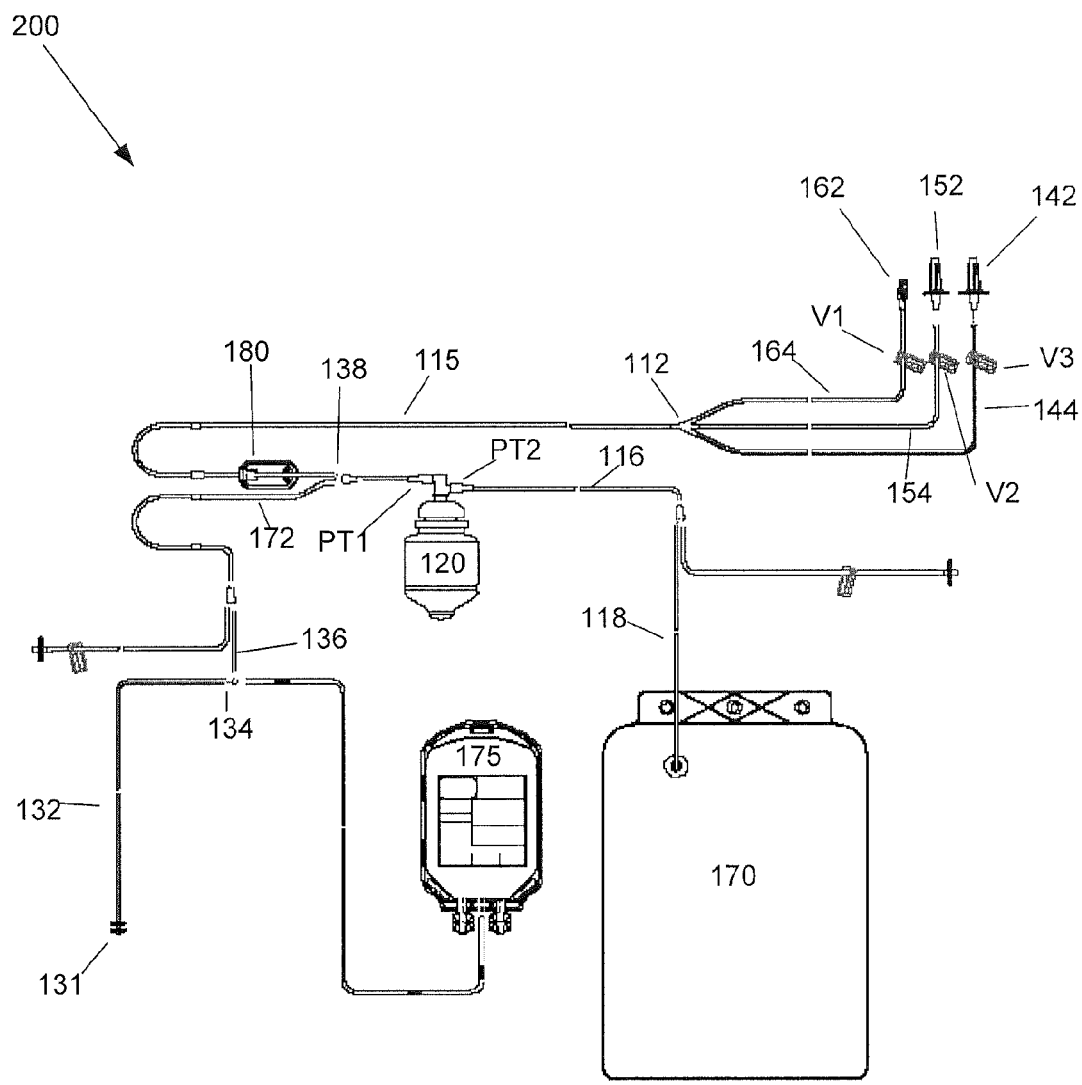
FIG. 2 is a schematic diagram of a disposable system for use with the system of FIG. 1, in accordance with one embodiment of the present invention.
Figure 3B:
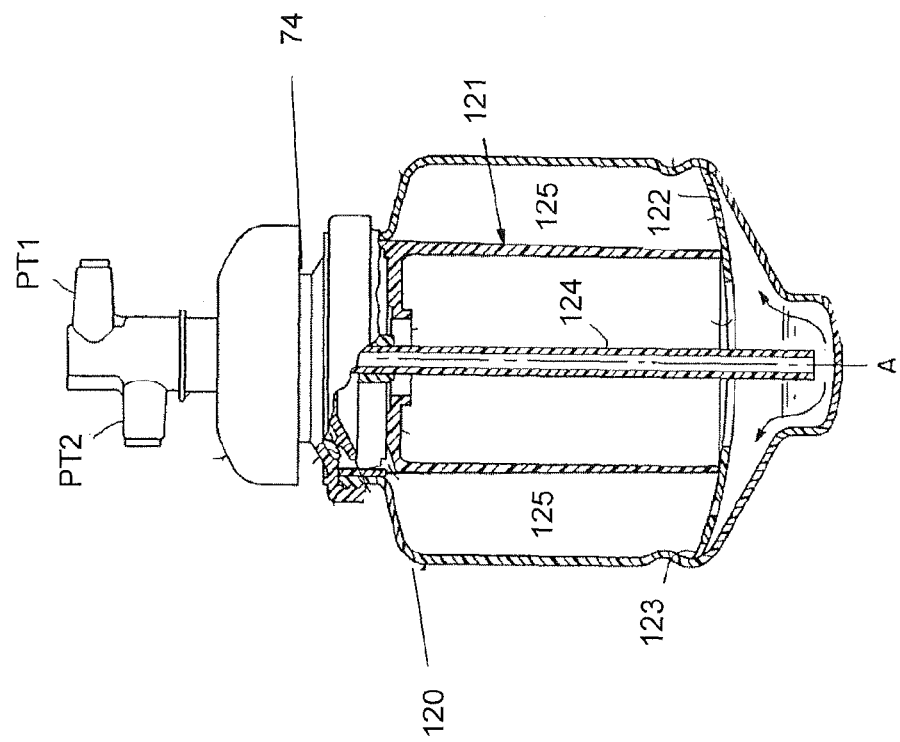
FIG. 3B schematically shows a side view of an alternative centrifuge bowl for use with the platelet wash system of FIG. 1, in accordance with some embodiments of the present invention.

Referring to FIGS. 1 and 2, an automated platelet wash system 100 uses a centrifuge 110, such as the centrifuge bowl described within U.S. Pat. No. 4,983,158, which is hereby incorporated by reference, to separate platelets from its supernatant (e.g., the fluid in which the platelets are suspended). Other types of separation chambers and devices may be used, such as, without limitation, a standard Latham type centrifuge (FIG. 3C), as described in U.S. Pat. Nos. 3,145,713 and 5,882,289, which are hereby incorporated by reference.

Figure 3A:
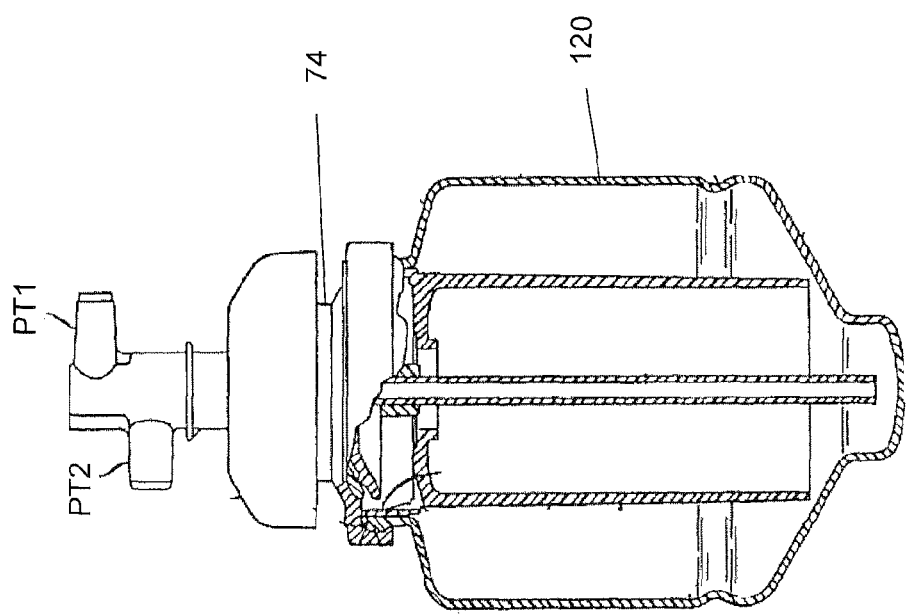
FIG. 3A schematically shows a side view of a centrifuge bowl for use with the platelet wash system of FIG. 1, in accordance with some embodiments of the present invention.
Figure 3C:
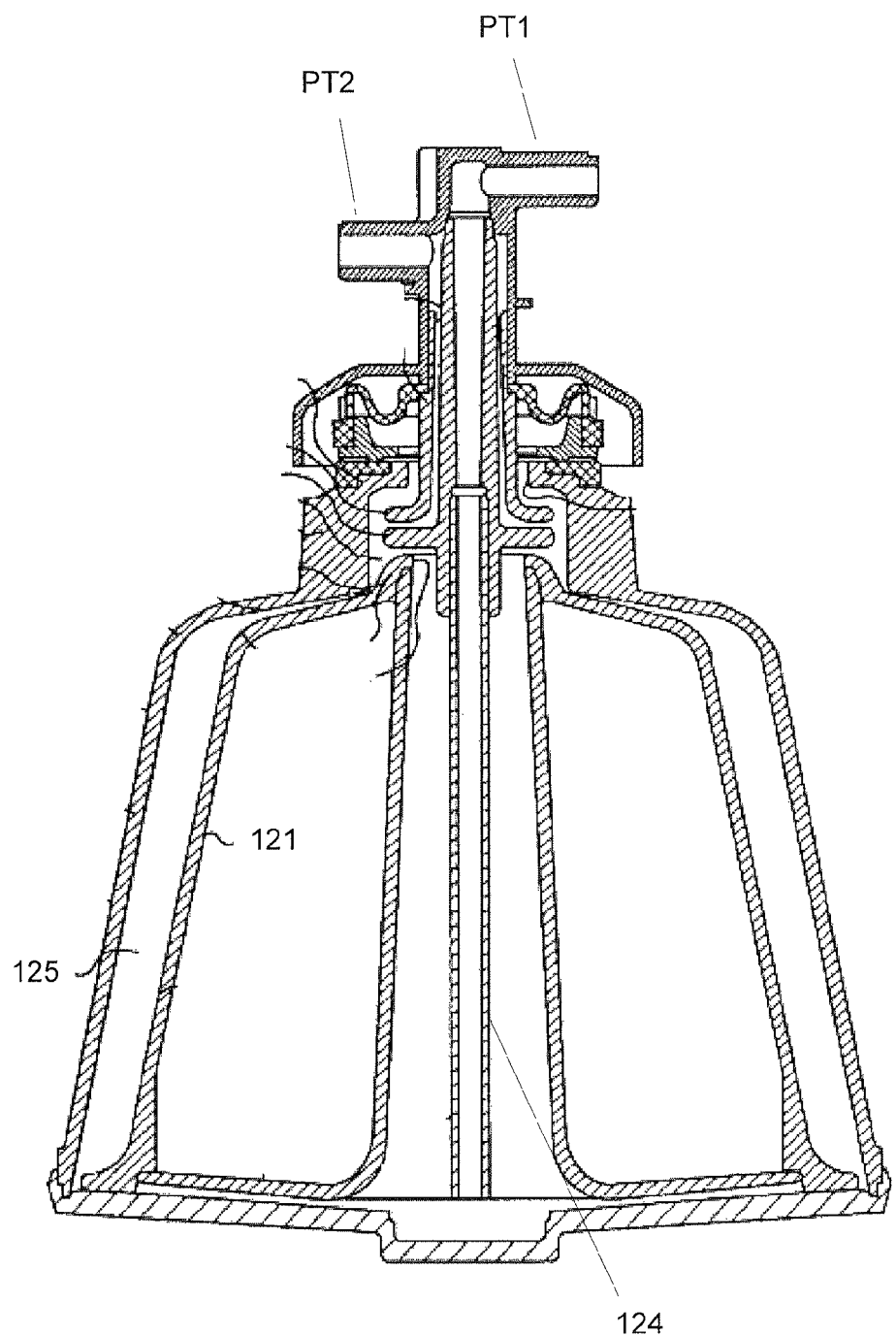
FIG. 3c schematically shows a side view of a third centrifuge bowl for use with the platelet wash system of FIG. 1, in accordance with some embodiments of the present invention.

The centrifuge 110 includes a rotating bowl 120 and stationary input and output ports PT1 and PT2 that are typically closely coupled to the bowl interior by a rotary seal 74 (see FIG. 3A). Although the material and size of the bowl 120 may vary depending upon the application and amount of platelet product to be washed, preferred embodiments of the present invention utilize bowls having volumes ranging from 210 to 275 ml and made from K-resin. Additionally, the system 100 may be a blood/cell processing system such as the ACP® 215 system by Haemonetics, Corp. and/or the red blood cell cryopreservation and recovery apparatus described in U.S. Pat. No. 6,440,372, which is hereby incorporated by reference.

As shown in FIG. 3B, in some embodiments, the centrifuge bowl 120 may include a core 121 with a diverter 122 located within the interior of the bowl 120, such as the centrifuge bowl described within U.S. Pat. No. 4,943,273, which is hereby incorporated by reference. The diverter 122 may be a donut-like member located near the bottom of the bowl 120 and may have openings 123 at the peripheral edge and openings 126 between the openings 123 and the core 121. As fluid to be processed (e.g., platelet product, PRP, etc.) enters the bowl 120 through input port PT1, the fluid flows through feed tube 124 and into the bottom of the bowl 120. The centrifugal forces then force the platelet product to flow outwardly and upwardly through openings 123 and into separation region 125. As wash solution (or platelet additive solution) enters the bowl 120, the wash solution may enter separation region 125 though openings 126 to create a washing cross-flow.

The input port PT1 of the centrifuge bowl 120 is in fluid communication with a platelet product container 130 via a tube 132, connector 134, tube 136, and a Y-connector 138. Tubes 132 and 136 have compatibility with blood and blood products, as is all the tubing in the system 100. The platelet product container 130 may contain platelet product (e.g., platelet rich plasma) derived from a donor using a blood apheresis system such as the MCS apheresis systems available from Haemonetics, Corp. As described in greater detail below, the inlet port PT1 is also fluidly connected to a variety of solution containers 140/150/160 (described in greater detail below) via valves V1/V2/V3, tubes 144/154/164, connector 112, and tube 115. The outlet port PT2 of the centrifuge bowl 120 is fluidly connected to a waste container 170 by a tube 116, a valve V4 and a tube 118.

As mentioned above, in addition to the platelet product container 130, the inlet port PT1 of the centrifuge 110 may also be fluidly connected to a number of solution containers 140/150/160. The solution containers may include a bag or container 140 for storing anticoagulant, a wash solution storage container 150, and a platelet additive solution storage container 160. The use of each of these solutions is described in greater detail below. The tube 115 connecting the solution containers 140/150/160 to the centrifuge bowl 120 may include a bacteria filter 180 that prevents any bacteria within the anticoagulant, platelet additive solution, and/or wash solution from entering the system 100. Containers 140/150/160 are preferably plastic bags made of material that is compatible with the solution that each bag contains.

The system 100 may also include a controller 190 that controls the overall operation of the system 100 and the centrifuge 110. For example, the controller 190 may control the operation of peristaltic pumps P1 and P2, as well as, valves V1/V2/V3/V4 to control the direction and duration of flow through the system 100. Additionally, the controller 190 may also control the operation of additional system components such as a shaker 192 and printer 194 (if equipped). The printer 194 may be used to print reports and/or other information regarding the process. As discussed in greater detail below, the shaker 192 may be used during the re-anticoagulation of the platelet product contained within container 130. The controller 190 may also be coupled to a display screen 196 that presents information to a system operator, and an input device 198 that allows the system operator to input information and supply the controller 190 with information. For example, the input device 198 may allow the user to input a desired final platelet volume (e.g., a volume greater than the bowl 120 volume) and/or a desired final platelet yield. As discussed in greater detail below, the controller 190 may add platelet additive solution to the washed-platelet product in order to achieve the desired volume and/or yield.

It is important to note that, in other embodiments of the present invention, the shaker 192 and the printer 194 may be stand alone components that are not connected to the system 100. In such embodiments, these components may operate independently from the system 100 and controller 190. For example, the shaker 192 may be an independent device with its own operational controls (e.g., it may not be controlled by controller 190).

In order to monitor the pressure within the system 100, the system may also include one or more pressure sensors. For example, the system 100 may include a pressure sensor 122 on tube 136 to measure the pressure between the pump P1 and the washed platelet collection bag 175. Similarly, the system 100 may also include a pressure sensor 126 on tube 118 to measure the pressure between the centrifuge bowl 120 and the waste container 170. Each of the pressure sensors 122/126 may include a filter 124/128 (e.g., a 0.2 µm hydrophobic filter and/or anti-bacterial filter) to preserve sterility within the system 100.

As shown in FIG. 2, various components may be packaged together as a disposable set 200. For example, the disposable set 200 may include tubes 115/116/118/132/144/154/172/174, connectors 134/138/112, valves V1/V2/V3/V4, the centrifuge bowl 120, the bacteria filter 180, the waste container 170, and the washed platelet storage container 175. Additionally, the disposable set 200 may also include connection ports for the solution containers 140/150/160, and the platelet product container 130. For example, the disposable set 200 may include a first sterile connection 131 for connecting the platelet product container 130, a second sterile connection 162 for connecting the platelet additive solution container 160, and connections 142/152 (e.g., spike connections, luer-lock connections, etc.) for connecting the wash solution container 150 and the anticoagulant container 140. Prior to starting the platelet wash procedure, the disposable set 200 may be removed from its packaging and installed into the system 100, as shown in FIG. 1.

Figure 4:
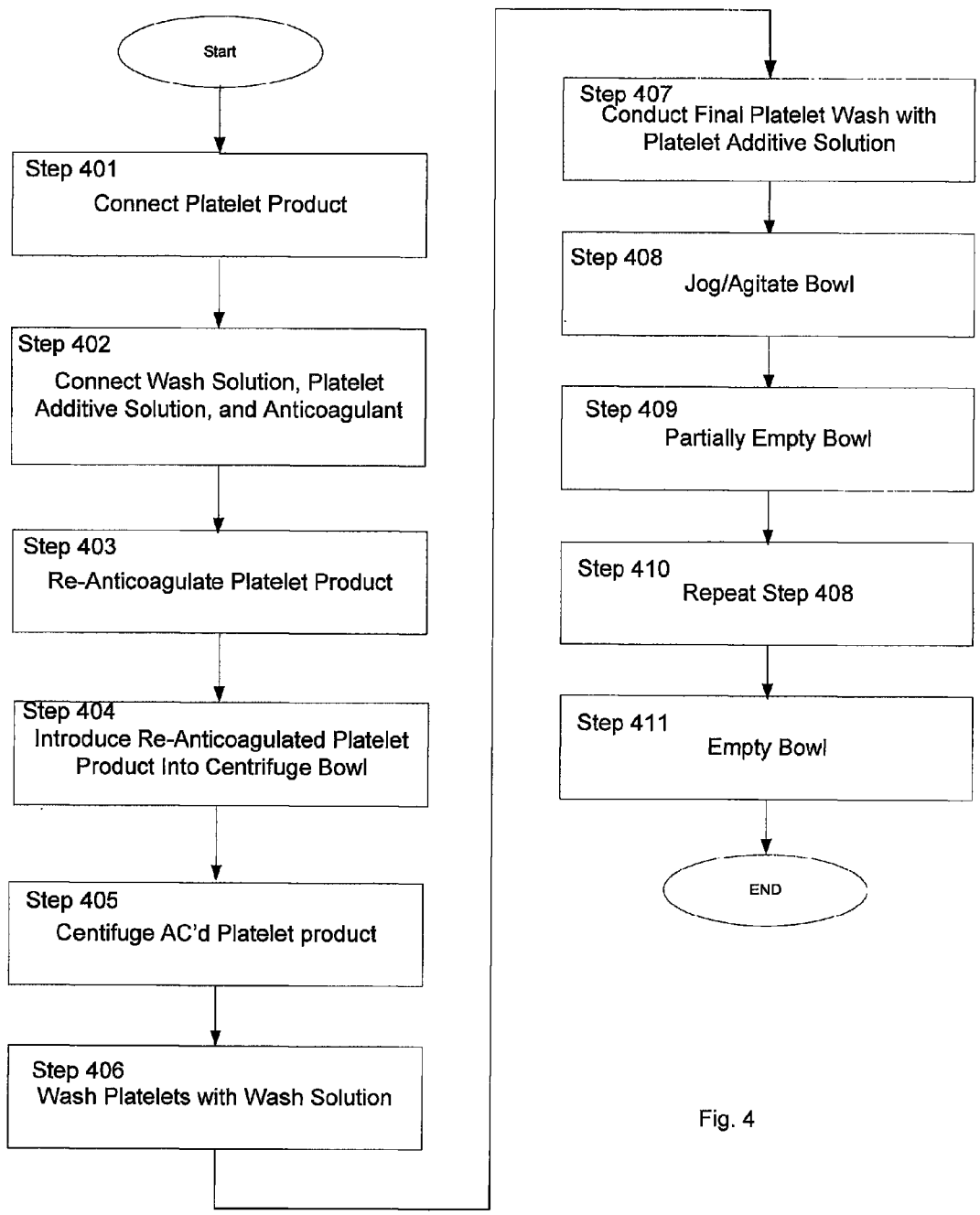
FIG. 4 is a flow chart depicting a method for washing collected platelets and platelet product, in accordance with one embodiment of the present invention.

FIG. 4 is a flowchart depicting a method for washing platelet product, in accordance with one embodiment of the invention. First, the system operator may connect the platelet product container 130 to the sterile port 131 (step 401) and connect the anticoagulant container 140, wash solution container 150, and platelet additive solution container 160 to connectors 142/152/162 (step 402). Once the containers are connected, the system 100 may add anticoagulant (e.g., to re-anticoagulate) to the platelet product within the platelet product container 130 (Step 403). To that end, the system 100 may energize pumps P1 and P2 and use the pumps P1/P2 (e.g., in series) to draw anticoagulant from container 140 through tubes 144 and 115, bacteria filter 180, lines 136, and 132 and into the platelet product container 130. In order to aid mixing of the platelet product and the anticoagulant, the platelet product container 130 may be placed on shaker 192 which agitates the solutions (e.g., the platelet product and the anticoagulant) within the platelet product container 130.

Once the anticoagulant is added to the platelet product, the system 100 may transfer a volume (e.g., all or part) of the re-anticoagulated platelet product to the centrifuge bowl 120 (Step 404) and begin to centrifuge the re-anticoagulated platelet product (step 405). Although the rate at which the platelet product is transferred to the centrifuge bowl 120 and the speed at which the bowl 120 is rotated (e.g., to centrifuge the platelet product) may vary, some embodiments of the present invention may transfer the platelet product at 150 ml/min and rotate the centrifuge bowl 120 at approximately 8000 RPM. As the platelet product enters the bowl 120 (e.g., separation region 125), the centrifugal forces on the platelet product will begin to separate the platelets from the supernatant (e.g., plasma) and cause the platelets to migrate towards the outer diameter of the bowl 120.

The system 100 may then continue to rotate the bowl 120 and begin to wash the platelets with wash solution (e.g., saline glucose) (Step 406). During this step, the pump P2 will begin to draw wash solution from container 150 and wash the platelets contained within the bowl 120 by introducing the wash solution into the centrifuge bowl 120 through inlet port PT1. As the wash solution enters the centrifuge bowl 120, the wash solution will begin to mix with the supernatant (e.g., the re-anticoagulated plasma) within the bowl 120 and separated from the platelets. As additional wash solution enters the bowl, the wash solution/plasma mixture will be displaced from the centrifuge bowl 120 through the outlet port PT2 and will be sent to the waste container 170 through tubes 116 and 118. Although the rate at which the system 100 introduces the wash solution to wash the platelets may also vary depending on the application and/or volume of platelet product being washed, some embodiments of the present invention wash the platelets at 150 ml/min for a total of 1500 ml of wash solution. Additionally, it is important to note that, during the wash step, the centrifuge 110 and bowl 120 continue to rotate at approximately 8000 RPM and the wash solution is continuously displaced (e.g., out port PT2 and into waste container 170) as additional wash solution is introduced into the bowl 120.

In some embodiments, it may be beneficial to add anticoagulant to the wash solution (e.g., a ratio of 1:20) prior to transferring the wash solution to the centrifuge bowl 120. To that end, the system 100/controller 190 may add anticoagulant to the wash solution at connector 112 and/or as it flows through line 115. For example, as pump P2 is drawing the wash solution from container 150, the controller 190 or system operator (if the valves are manual valves) may open and close valve V1 at appropriate intervals to meter anticoagulant into lines 144 and 115 as the wash solution is being transferred to the bowl 120.

It is important to note that, by adding anticoagulant to the platelet product and the wash solution, the pH of the platelets and contents of the bowl 120 temporarily decrease (e.g., while the platelets are being washed with the wash solution). This temporary decrease in pH helps prevent the platelets from adhering to each other during processing. Additionally, as discussed in greater detail below, the pH of the final platelet product (e.g., the washed platelets) increases (e.g., to above 6.4) once the platelets are resuspended in the platelet additive solution.

After the system 100 performs the initial wash step (e.g., Step 406) with wash solution, the system 100 will then begin the final platelet wash (Step 407). During the final platelet wash, the system 100 will close valve V2 and open V3 in order to transfer the platelet additive solution from container 160 to the centrifuge bowl 120. As the platelet additive solution is transferred to the centrifuge bowl 120, the platelet additive solution will mix with the wash solution remaining within the bowl from the initial wash step (e.g., Step 406). Additionally, in a manner similar to the initial wash step with the wash solution (e.g., Step 406), the system 100 will transfer a greater volume of platelet additive solution than the centrifuge bowl 120 can hold. For example, the final wash step may transfer 500 ml of platelet additive solution at 150 ml/min while the bowl 120 is rotating at approximately 8000 RPM. However, as platelet additive solution enters the bowl 120 through the inlet port PT1, an equivalent volume of the platelet additive solution/wash solution mixture will be displaced through outlet PT2 and flow into the waste container 170. Once the final wash step is complete, the system 100/controller 190 may stop the centrifuge.

After completing the final wash (Step 407) and stopping the centrifuge 110 and bowl 120, the system 100/controller 190 may agitate and/or jog the bowl 120 (Step 408 to help remove any platelets that may be stuck to the side of the centrifuge bowl 120 by commencing a series of acceleration and deceleration steps prior to emptying the bowl 120. For example, the controller 190 may start/accelerate the centrifuge 110/bowl 120 for a predetermined amount of time (e.g., 2 seconds) and then decelerate the centrifuge 110/bowl 120. The jogging (e.g., the alternating acceleration and deceleration) creates turbulence within the bowl 120 and induces movement of the fluid in the bowl 120 relative to the bowl 120 which, in turn, helps remove the platelets from the wall of the bowl 120. The system 100/controller 190 may repeat this acceleration/deceleration process multiple time (e.g., 3 additional times).

It is important to note that, in some embodiments, the controller 190 does not need to stop the bowl between the acceleration and deceleration steps. For example, the controller 190 does not need to allow the bowl 120 come to a complete stop during the deceleration step before accelerating the bowl 120. Additionally, to decelerate the bowl 120, the controller may simply de-energize the bowl 120/centrifuge 110 and allow the bowl 120 to decelerate on its own (e.g., by the friction within the motor, bowl 120, etc.). In other words, in some embodiments, the controller 120 does not have to actively brake the bowl 120 during deceleration.

In some embodiments, the acceleration and deceleration steps may include starting and stopping the bowl 120. For example, the initial acceleration step may start the bowl 120 from a stop. In such embodiments, the controller 190 may also bring the bowl 120 to a complete stop (or allow the bowl 120 to come to a complete stop) during the deceleration step.

Once the initial agitation step is complete (Step 408), the system 100/controller 190 may partially empty the bowl 120 (Step 409) by using pump P1 to remove a volume of the platelet additive solution and platelets from the bowl 120, and transfer the volume to the washed platelet storage container 175. By reducing the volume within the centrifuge bowl 120, the "sloshing" and turbulence within the bowl 120 is increased during subsequent agitation steps, discussed below.

The system 100/controller 190 may then begin a second jogging/agitation step (Step 410) in which the system 100/controller 190 repeats the agitation process (Step 408). For example, the system 100/controller 190 may, once again, accelerate and decelerate (e.g., starts and stops) the bowl 120 multiple times in order create turbulence within the bowl 120 and remove the platelets from the walls of the bowl 120. Additionally, like the first agitation step (Step 408), the controller may accelerate the bowl for predetermined period of time (e.g., 2 seconds) and decelerate the bowl 12 repeatedly (e.g., four times total).

The direction of rotation of the centrifuge 110 and bowl 120 may depend upon the type of system 100 and centrifuge 110 used. For example, if equipped with a dual-direction centrifuge, the system 100/controller 190 may alternate the direction of rotation for each acceleration/start cycle. In other words, the system 100/controller 190 may alternate rotating the bowl 120 in clock-wise and counter-clock-wise directions (e.g., in order to increase the turbulence within the bowl 120). Additionally, although the agitation steps are described above as accelerating/starting the centrifuge 110 for two seconds and repeating three times (e.g., for a total of four start/stop cycles), the time and number of repeats can vary. For example, some embodiments of the invention may accelerate/start the centrifuge for three seconds and other embodiments may start the centrifuge 110 for one or four or more seconds. Likewise, some embodiments may only repeat the acceleration/deceleration steps twice and other embodiments may repeat four or more times.

Once the second jogging/agitation step (Step 410) is complete, the system 100/controller 190 may stop the centrifuge 110 and empty the bowl 120 (Step 411). For example, the controller 190 may energize pump P2 and draw the remaining platelets and platelet additive solution through the inlet port PT1 and transfer the platelets/platelet additive solution to the washed platelet storage container 175.

As mentioned above, the addition of anticoagulant to the platelet product and wash solution reduces the pH of the platelets and platelet product during washing. However, once the platelet additive solution displaces the wash solution within the bowl 120 and the platelets are resuspended in the platelet additive solution, the pH increases to a level more suitable for platelet storage (e.g., above 6.4 and/or the pH of the platelet additive solution).

Figure 5:
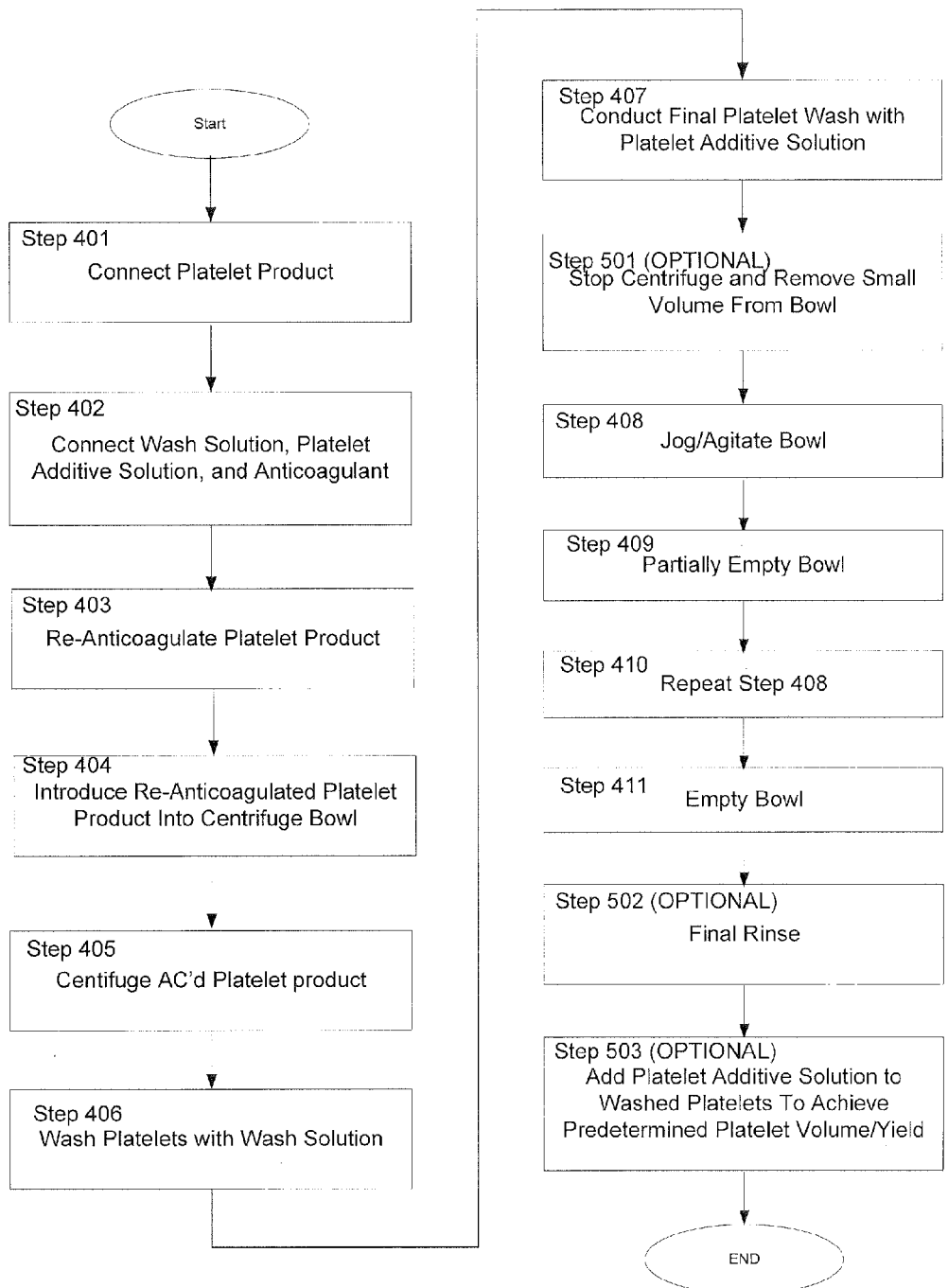
FIG. 5 is a flow chart depicting an alternative method for washing collected platelets and platelet product, in accordance with additional embodiments of the present invention.

In addition to the steps described above and shown in FIG. 4, some embodiments may also include additional, optional steps. For example, as shown in FIG. 5, prior to starting the initial jogging/agitation step (Step 408), some embodiments may stop the centrifuge 110 and transfer a small volume (e.g., 50 ml) of platelet additive solution and platelets from the bowl 120 to the washed platelet storage container 175 (Step 501). By doing so, the system 100 may improve the "sloshing" and turbulence within the bowl 120 which, in turn, helps remove the platelets from the walls of the centrifuge bowl 120.

Additionally or alternatively, some embodiments may conduct a final rinse step (Step 502) after emptying the bowl 120 (e.g., after Step 411). During the final rinse step, the system 100/controller 190 may transfer a volume (e.g., 35 ml) of platelet additive solution to the centrifuge bowl 120. The system 100/controller 190 may then accelerate and decelerate (e.g., start and stop) the bowl 120 in a manner similar to steps 408 and 410 to rinse out any remaining platelets contained with bowl 120. This rinse may then be transferred to the washed platelet storage container 175.

Furthermore, if the operator input a desired platelet volume or desired platelet yield into the input device 198 (discussed above), the controller 190 may add platelet additive solution to the washed-platelet product within collection bag 175 to obtain the programmed volume or yield (Step 503). For example, the controller 190 may use pumps P1 and P2 (e.g., in series) to transfer the required volume of platelet additive solution from container 160 to the collection container 175.

It is also important to note that the flow rates and volumes discussed above are only meant as examples, and the flow rates and volumes may vary. For example, the wash solution flow rate and volume may be greater than or less than 150 ml/min and 1500 ml, respectively. Additionally, the platelet additive solution flow rate and volume may be greater than or less than 150 ml/min and 500 ml, respectively. Furthermore, the RPM provided above is similarly meant only as an example and may vary. For example, the RPM may be less than or greater than 8000 RPM (e.g., it may be between 7000 and 7500 RPM, less than 7000 RPM, or greater than 8000 RPM).

The systems and methods described above provide numerous advantages over the prior art. In particular, because embodiments of the present invention are conducted within a closed system, there is a reduced risk of contamination and the final product (e.g., the washed platelets) can be stored for greater periods of time. For example, platelets washed with embodiments of the present invention may be stored for greater than 24, as compared to only 6-8 hours for platelets washed with the prior art manual procedures described above.

Additionally, because various embodiments of the present invention are automated, the results (e.g., platelet recovery, protein removal, etc.) are reproducible and less subject to operator error. For example, embodiments of the present invention are repeatedly able to reduce the protein within the platelet product by greater than 80% (and up to 99%) and repeatedly recover greater than 80% of the platelets within the initial platelet product (e.g., the PRP).

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A system for automated platelet washing comprising:
   a sterile connection for connecting a platelet product container to the system, and withdrawing platelet product from the platelet product container;
   a centrifuge bowl for separating the platelet product into platelets and a supernatant, the centrifuge bowl configured to send the supernatant to a waste container;
   a wash solution source fluidly connected to the centrifuge bowl and configured to send wash solution to the centrifuge bowl;
   a platelet additive solution source fluidly connected to the centrifuge bowl and configured to send platelet additive solution to the centrifuge bowl; and
   a controller configured to control the operation of the centrifuge bowl, the controller configured to remove a volume of platelet additive solution and platelets within the centrifuge bowl to a washed platelet container and jog the centrifuge bowl by accelerating and decelerating the centrifuge bowl multiple times to resuspend the platelets within the platelet additive solution after the platelet additive solution is added to the platelets and the supernatant is sent to the waste container.

2. A system according to claim 1, wherein accelerating the centrifuge bowl includes starting the centrifuge bowl from a stop and decelerating the centrifuge bowl includes stopping the centrifuge bowl.

3. A system according to claim 2, wherein the controller alternates starting the bowl in clockwise and counter-clockwise directions when starting and stopping the centrifuge bowl.

4. A system according to claim 1, wherein the controller accelerates and decelerates the centrifuge bowl four times.

5. A system according to claim 1, wherein the system is configured to transfer a portion of the resuspended platelets to the washed platelet container after the controller jogs the centrifuge bowl.

6. A system according to claim 5, wherein the controller is configured to repeat the jogging of the centrifuge bowl after the portion of the resuspended platelets is transferred to the washed platelet container.

7. A system according to claim 1, wherein the system transfers the remaining platelets and platelet additive solution to the washed platelet container after the controller jogs the centrifuge bowl.

8. A system according to claim 7, wherein the controller is further configured to add platelet additive solution to the washed-platelet storage container after the system transfers the remaining platelets and platelet additive solution to the washed platelet container to achieve a predetermined washed-platelet volume.

9. A system according to claim 7, wherein the controller is further configured to add platelet additive solution to the washed-platelet storage container after the system transfers the remaining platelets and platelet additive solution to the washed platelet container to achieve a predetermined washed-platelet yield.

10. A system according to claim 1, wherein the platelet product is platelet rich plasma and the supernatant is plasma.

11. A system according to claim 1, wherein the controller accelerates the centrifuge bowl for two seconds prior to stopping the bowl.

12. A system according to claim 1, wherein the wash solution is anticoagulated saline glucose.

13. A system according to claim 1 further comprising an anticoagulant source, the system introducing anticoagulant from the anticoagulant source into the platelet product container.

* * * * *